US00PP20547P2

(12) United States Plant Patent
Bergman

(10) Patent No.: US PP20,547 P2
(45) Date of Patent: Dec. 8, 2009

(54) ***CHRYSANTHEMUM* PLANT NAMED 'PINK YOSONOMA'**

(50) Latin Name: *Chrysanthemum×morifolium*
Varietal Denomination: Pink Yosonoma

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/283,270

(22) Filed: Sep. 8, 2008

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP12,906 P2 * 9/2002 Vandenberg et al. ..... Plt./286
PP17,860 P2 * 7/2007 Bergman ..... Plt./286

OTHER PUBLICATIONS

Plant Varieties Journal No. 68 Jul. 2008. 112 pages, see especially p. 13.*

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Pink Yosonoma', characterized by its upright, outwardly spreading and uniformly mounded plant habit; strong and vigorous growth habit; freely branching habit; dark green-colored foliage; uniform, freely and early flowering habit; daisy-type inflorescences with light purple-colored ray florets; and excellent postproduction longevity.

1 Drawing Sheet

Botanical designation: *Chrysanthemum×morifolium.*
Cultivar denomination: 'Pink Yosonoma'.

CROSS-REFERENCED TO CLOSELY RELATED APPLICATIONS

Title: *Chrysanthemum* Plant Named 'Red Yosonoma' U.S. Plant patent application Ser. No. 12/283,269.
Applicant: Wendy R. Bergman.

BACKGROUND OF THE INVENTION

The present invention relates to a new and distinct cultivar of *Chrysanthemum* plant, botanically known as *Chrysanthemum×morifolium*, commercially grown as a pot-type *Chrysanthemum* and hereinafter referred to by the name 'Pink Yosonoma'.

The new *Chrysanthemum* is a naturally-occurring whole plant mutation of the *Chrysanthemum×morifolium* cultivar 'Yosonoma', disclosed in U.S. Plant Pat. No. 17,860. The new *Chrysanthemum* was discovered and selected by the Inventor in a controlled greenhouse environment as a single flowering plant within a population of plants of 'Yosonoma' in December, 2005, in Fort Myers, Fla.

Asexual reproduction of the new *Chrysanthemum* by vegetative tip cuttings was first conducted in a controlled greenhouse environment in Fort Myers, Fla. in March, 2006. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pink Yosonoma'. These characteristics in combination distinguish 'Pink Yosonoma' as a new and distinct pot-type *Chrysanthemum* cultivar:

1. Upright, outwardly spreading and uniformly mounded plant habit.
2. Strong and vigorous growth habit.
3. Freely branching habit.
4. Dark green-colored foliage.
5. Uniform, freely and early flowering habit.
6. Daisy-type inflorescences with light purple-colored ray florets.
7. Excellent postproduction longevity with inflorescences maintaining good substance and color for about five to six weeks in an interior environment.

Plants of the new *Chrysanthemum* differ from plants of the parent, 'Yosonoma', in the following characteristics:

1. Plants of the new *Chrysanthemum* flower more uniformly than plants of 'Yosonoma'.
2. Plants of the new *Chrysanthemum* and 'Yosonoma' differ in ray floret color as plants of 'Yosonoma' have darker purple-colored ray florets.

Plants of the new *Chrysanthemum* differ from plants of *Chrysanthemum×morifolium* 'Red Yosonoma', disclosed in U.S. Plant patent application Ser. No. 12/283,269, primarily in ray floret color as plants of 'Red Yosonoma' have cherry red-colored ray florets.

Plants of the new *Chrysanthemum* can be compared to plants of *Chrysanthemum×morifolium* 'Yoroanoke', disclosed in U.S. Plant Pat. No. 12,906. In side-by-side comparisons conducted in Fort Myers, Fla., plants of the new *Chrysanthemum* primarily from plants of 'Yoroanoke' in the following characteristics:

1. Plants of the new *Chrysanthemum* had larger inflorescences than plants of 'Yoroanoke'.
2. Plants of the new *Chrysanthemum* flowered about one week later than plants of 'Yoroanoke'.
3. Plants of the new *Chrysanthemum* and 'Yoroanoke' differed in ray floret color as plants of 'Yoroanoke' had lavender pink-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of typical flowering plants of 'Pink Yosonoma' grown in a container.

The photograph at the top of the sheet is a close-up view of typical inflorescences of 'Pink Yosonoma'.

DETAILED BOTANICAL DESCRIPTION

The aforementioned photographs and following observations and measurements describe plants grown in Leamington, Ontario, Canada during the late spring in a glass-covered greenhouse and under conditions and practices which approximate those generally used in commercial pot-type *Chrysanthemum* production. During the production of the plants, day temperatures ranged from 20° C. to 24° C., night temperatures ranged from 15° C. to 17° C. and light levels ranged from 4,000 to 6,000 foot candles. Four unrooted cuttings were directly stuck in 15-containers, exposed to long day/short night conditions, and pinched about three weeks later. At the time of the pinch, the photoinductive short day/long night treatments were started. Plants used in the photographs and for the description had been growing for eleven weeks and were grown as spray-types. In the following description, color references are made to The Royal Horticultural Society Colour Chart, 2001 Edition, except where general terms of ordinary dictionary significance are used.

Botanical classification: *Chrysanthemum×morifolium* 'Pink Yosonoma'.

Parentage: Naturally-occurring whole plant mutation of *Chrysanthemum×morifolium* 'Yosonoma', disclosed in U.S. Plant Pat. No. 17,860.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description: Appearance: Herbaceous daisy pot-type *Chrysanthemum* typically grown as a natural spray type. Stems upright and outwardly spreading giving a uniformly mounded appearance to the plant. Freely branching habit, about five to six lateral branches develop after removal of terminal apex (pinching); dense and full plant habit. Strong and vigorous growth habit.

*Plant height.*—About 27.5 cm.

*Plant width.*—About 25 cm.

*Lateral branches.*—Length: About 22 cm. Diameter: About 3.5 mm. Internode length: About 2.5 cm. Strength: Strong. Texture: Pubescent; longitudinally ridged. Color: Close to 148B.

Foliage description:

*Arrangement.*—Alternate, simple.

*Length.*—About 7.4 cm.

*Width.*—About 4.3 cm.

*Shape.*—Palmately lobed.

*Apex.*—Cuspidate.

*Base.*—Attenuate.

*Margin.*—Palmately lobed, sinuses between lateral lobes parallel.

*Texture, upper and lower surfaces.*—Fine pubescence; veins prominent on lower surface.

*Color.*—Developing leaves, upper surface: Close to N137A. Developing leaves, lower surface: Close to 137B. Fully expanded leaves, upper surface: Close to 147A; venation, close to 147B. Fully expanded leaves, lower surface: Close to 137A; venation, close to 147B.

*Petiole.*—Length: About 2 cm. Diameter: About 2 mm. Texture, upper and lower surfaces: Pubescent. Color, upper and lower surfaces: Close to 147B.

Inflorescence description:

*Appearance.*—Daisy-type inflorescence form with elongated oblong-shaped ray florets. Inflorescences borne on terminals above foliage. Disc and ray florets arranged acropetally on a capitulum. Typically grown as a spray-type.

*Fragrance.*—Not detected.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about nine weeks later.

*Postproduction longevity.*—Inflorescences maintain good color and substance for about five to six weeks in an interior environment; inflorescences persistent.

*Quantity of inflorescences.*—Freely flowering, about five to seven inflorescences develop per lateral stem.

*Inflorescence bud.*—Height: About 1.8 cm. Diameter: About 1.2 cm. Shape: Ovoid. Color: Close to N77D.

*Inflorescence size.*—Diameter: About 7.5 cm. Depth (height): About 3 cm. Diameter of disc: About 1.4 cm. Receptacle height: About 1 cm. Receptacle diameter: About 2 cm. Receptacle color: Close to 137A.

*Ray florets.*—Shape: Elongated oblong. Orientation: Initially upright, with development, close to 55° to 65° from vertical. Aspect: Reflexed. Length: About 4.2 cm. Width: About 8 mm. Apex: Acute or emarginate. Base: Attenuate; short corolla tube. Margin: Entire. Texture, upper and lower surfaces: Smooth, glabrous; velvety. Number of ray florets per inflorescence: About 45 arranged in about three whorls. Color: When opening, upper surface: Close to 70A. When opening, lower surface: Close to 77D. Fully opened, upper surface: Close to 70B; color does not fade with development. Fully opened, lower surface: Close to 84C; color does not fade with development.

*Disc florets.*—Arrangement: Massed at center of receptacle. Shape: Tubular, elongated. Apex: Five-pointed. Length: About 6 mm. Diameter: About 1.5 mm. Number of disc florets per inflorescence: About 238. Color, immature: Apex: Close to 151C. Mid-section: Close to 145C. Base: Close to 145D. Color, mature: Apex: Close to 1A. Mid-section: Close to 145C. Base: Close to 145B.

*Phyllaries.*—Number of phyllaries per inflorescence: About 24 arranged in about two whorls. Length: About 8 mm. Width: About 2 mm. Shape: Narrowly elliptical. Apex: Acute. Base: Truncate. Margin: Entire. Texture, upper surface: Smooth, glabrous; waxy. Texture, lower surface: Pubescent. Color, upper and lower surfaces: Close to 146A.

*Peduncles.*—Length: About 7 cm to 7.5 cm. Diameter: About 2.5 mm. Angle: About 45° from vertical. Strength: Strong, flexible. Texture: Pubescent. Color: Close to 147B.

*Reproductive organs.*—Androecium: Present on disc florets only. Filament length: About 1.5 mm. Filament color: Close to 157D. Anther shape: Oblong. Anther length: About 2 mm. Anther color: Close to 12A. Pollen amount: None observed. Gynoecium: Present on both ray and disc florets. Pistil length: About 5 mm. Stigma shape: Bi-parted. Stigma color: Close to 3A. Style length: About 3 mm. Style color: Close to 150C. Ovary color: Close to 155D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Pink Yosonoma' as illustrated and described.

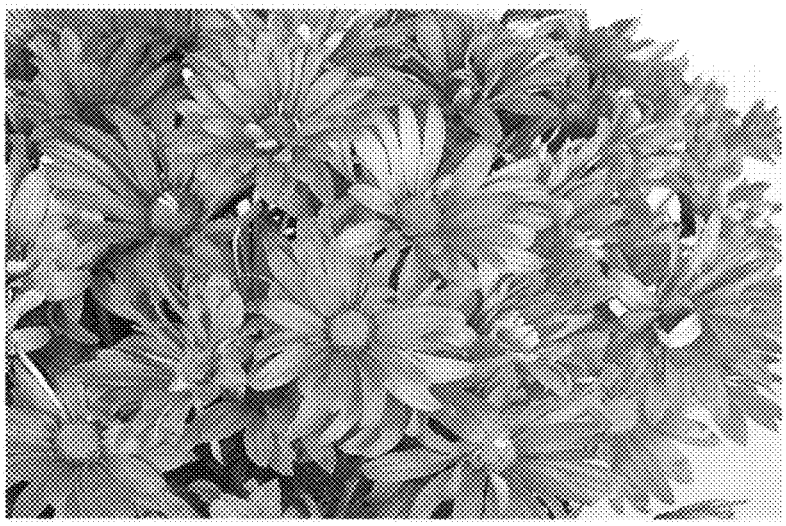
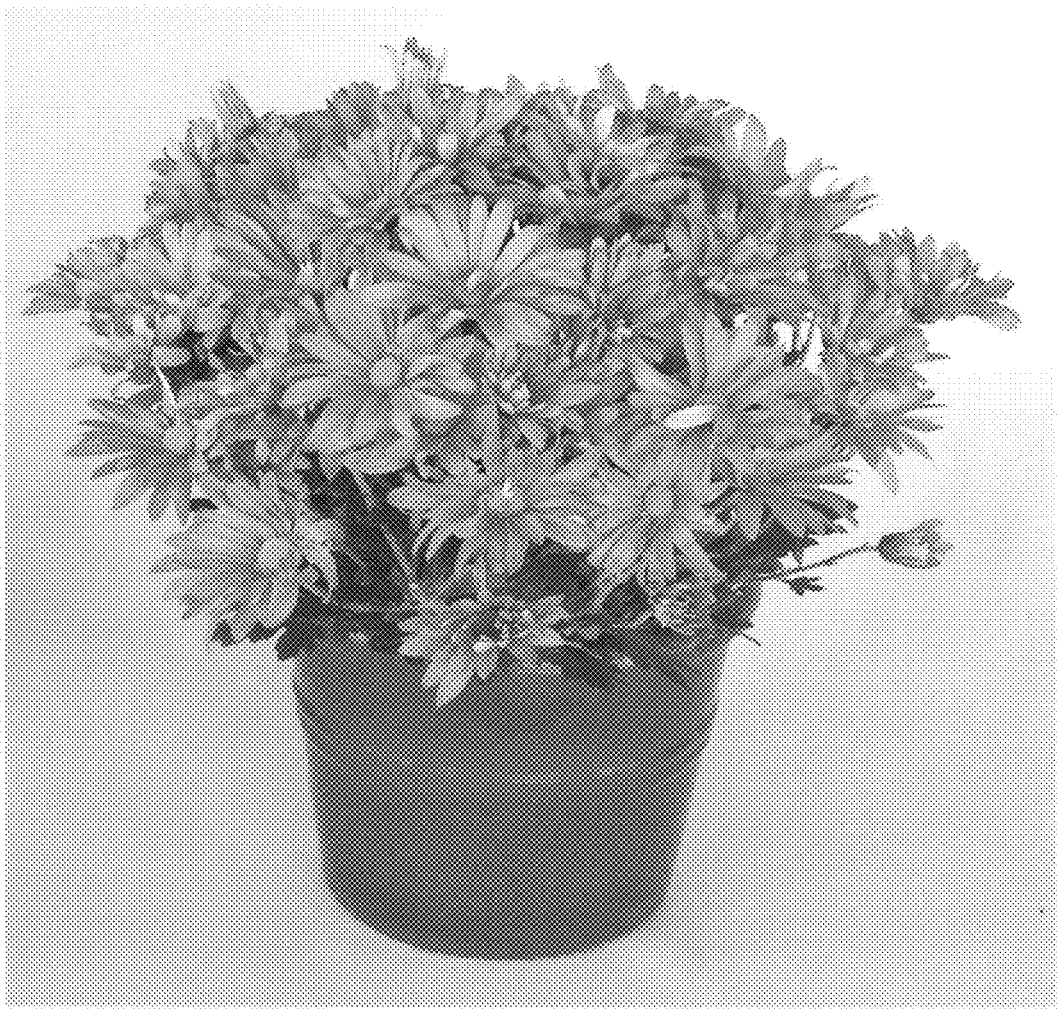

* * * * *